United States Patent
Murase et al.

(10) Patent No.: US 10,145,538 B2
(45) Date of Patent: Dec. 4, 2018

(54) LIGHT-EMITTING APPARATUS, CALIBRATION COEFFICIENT CALCULATION METHOD, AND METHOD FOR CALIBRATING CAPTURED IMAGE OF EXAMINATION TARGET ITEM

(71) Applicant: IIX INC., Tokyo (JP)

(72) Inventors: Hiroshi Murase, Tokyo (JP);
Tomoyuki Takano, Tokyo (JP)

(73) Assignee: IIX INC., Tokyo (JP)

( * ) Notice: Subject to any disclaimer, the term of this patent is extended or adjusted under 35 U.S.C. 154(b) by 0 days.

(21) Appl. No.: 15/545,982

(22) PCT Filed: Jan. 27, 2016

(86) PCT No.: PCT/JP2016/052244
§ 371 (c)(1),
(2) Date: Jul. 24, 2017

(87) PCT Pub. No.: WO2016/125643
PCT Pub. Date: Aug. 11, 2016

(65) Prior Publication Data
US 2018/0010767 A1 Jan. 11, 2018

(30) Foreign Application Priority Data
Feb. 2, 2015 (WO) .................. PCT/JP2015/052840

(51) Int. Cl.
F21V 11/00 (2015.01)
F21V 9/08 (2018.01)
(Continued)

(52) U.S. Cl.
CPC .................. *F21V 9/08* (2013.01); *F21K 9/64* (2016.08); *G01C 11/025* (2013.01);
(Continued)

(58) Field of Classification Search
USPC .................................. 362/351; 235/454, 455
See application file for complete search history.

(56) References Cited

U.S. PATENT DOCUMENTS

2005/0254704 A1* 11/2005 Komiya ............... H04N 5/2256
382/162
2008/0137324 A1* 6/2008 Pastore .................. G03B 15/06
362/16
(Continued)

FOREIGN PATENT DOCUMENTS

JP 2002181659 A 6/2002
JP 2007057421 A 3/2007
(Continued)

OTHER PUBLICATIONS

ISA Japan Patent Office, International Search Report Issued in PCT Application No. PCT/JP2016/052244, dated Mar. 1, 2016, WIPO, 4 pages.

*Primary Examiner* — Tuyen K Vo
(74) *Attorney, Agent, or Firm* — Alleman Hall Creasman & Tuttle LLP

(57) ABSTRACT

Provided are a light-emitting apparatus that can suppress manufacturing cost to a low level and perform light emission with high uniformity using a simple configuration, a calibration coefficient calculation method using the light-emitting apparatus, and a method for calibrating a captured image of an inspection target object. A plurality of light-emitting diodes arranged at equal intervals on the circumference of a virtual circle, and a milky white-colored emission window, which is provided on a top surface portion separated from the light-emitting diodes, has an outer edge that is smaller than the circumference on which the light-emitting diodes are arranged, and allows light of the light-emitting diodes to pass therethrough, are included. The diameter of the virtual circle on which the light-emitting (Continued)

diodes are arranged and a separation distance between the light-emitting diodes and the emission window are set to predetermined distances.

9 Claims, 13 Drawing Sheets

(51) Int. Cl.
| | |
|---|---|
| *F21K 9/64* | (2016.01) |
| *G01C 11/02* | (2006.01) |
| *G06T 5/00* | (2006.01) |
| *G02F 1/13* | (2006.01) |
| *G02F 1/13357* | (2006.01) |
| *H04N 17/00* | (2006.01) |
| *F21Y 113/13* | (2016.01) |
| *F21Y 115/10* | (2016.01) |
| *F21K 99/00* | (2016.01) |
| *G01N 21/93* | (2006.01) |

(52) U.S. Cl.
CPC .......... *G02F 1/1309* (2013.01); *G02F 1/1336* (2013.01); *G06T 5/008* (2013.01); *H04N 17/002* (2013.01); *F21K 2099/005* (2013.01); *F21Y 2113/13* (2016.08); *F21Y 2115/10* (2016.08); *G01N 21/93* (2013.01); *G06T 2207/10148* (2013.01); *G06T 2207/30121* (2013.01)

(56) References Cited

U.S. PATENT DOCUMENTS

| | | | |
|---|---|---|---|
| 2008/0253123 A1* | 10/2008 | Miyasu | G03B 21/2086 362/285 |
| 2009/0045245 A1* | 2/2009 | Yamamoto | B23K 1/018 228/119 |
| 2009/0258684 A1* | 10/2009 | Missotten | G01N 21/85 460/5 |
| 2012/0187836 A1* | 7/2012 | Hashimoto | F21V 5/04 315/51 |
| 2012/0256533 A1* | 10/2012 | Seto | C04B 35/58085 313/498 |
| 2013/0128570 A1* | 5/2013 | Jiang | F21V 5/04 362/235 |

FOREIGN PATENT DOCUMENTS

| | | |
|---|---|---|
| JP | 2007158577 A | 6/2007 |
| JP | 2008083256 A | 4/2008 |
| JP | 2009145180 A | 7/2009 |
| JP | 2009174857 A | 8/2009 |
| JP | 2012013474 A | 1/2012 |

* cited by examiner

Radius $l_1$ : Distance $d$ = 1 : 0.5

Radius $l_1$ : Distance $d$ = 1 : 1

LIGHT-EMITTING APPARATUS, CALIBRATION COEFFICIENT CALCULATION METHOD, AND METHOD FOR CALIBRATING CAPTURED IMAGE OF EXAMINATION TARGET ITEM

TECHNICAL FIELD

The present invention relates to a light-emitting apparatus, a calibration coefficient calculation method performed using the light-emitting apparatus, and a method for calibrating a captured image of an inspection target object, in which a captured image of an inspection target object is calibrated based on a calculated calibration coefficient.

BACKGROUND ART

With a display panel such as a liquid crystal panel or an organic EL panel, in general, display unevenness sometimes occurs due to variations in machining accuracy in a manufacturing step. Accordingly, before the display panel is shipped, an inspection for detecting display unevenness of the display panel is performed.

In the inspection, the pixels of the display panel are illuminated, the pixels are imaged using a camera including a solid-state image sensor so as to measure the luminance of the pixels, and thereby display unevenness is detected. The detected display unevenness is corrected, whereby an improvement in the quality of the display panel is achieved.

On the other hand, the solid-state image sensor of the camera varies in sensitivity, and furthermore, the amount of light received by the solid-state image sensor through the lens of the camera tends to be smaller if it is received from the peripheral portions of the lens in comparison to being received from the central portion of the lens, and thus a difference in brightness occurs between the central portion and the peripheral portion.

In this way, if there is variation in the sensitivity of the solid-state image sensor in the camera that performs the inspection and the amount of light received by the solid-state image sensor via the lens differs between elements, even if there is no defect in the display panel that is to be inspected, unevenness that does not actually exist in the display panel is imaged in the captured image of the display panel imaged by the camera and it is not possible to obtain a correct inspection result for the display panel in some cases.

As a countermeasure against this, Patent Document 1 discloses a captured image calibration method that aims to calibrate a captured image of a display panel that is an inspection target object, based on a calibration coefficient for calibrating sensitivity variations or the like of a solid-state image sensor.

According to the captured image calibration method in Patent Document 1, sample light emitted from an emission window of an integration sphere provided with a light source is imaged with the camera, and a calibration coefficient is created based on the imaged data of the imaged sample light. The captured image of the display panel that is the inspection target object is calibrated based on the calibration coefficient.

The integration sphere used in this calibration method has a hollow sphere body with an inner surface on which a diffuse reflection material is applied, the light emitted by a light source is reflected by the diffuse reflection material in the sphere body, and the sample light is emitted with a uniform luminance distribution from the emission window of the integration sphere to the surface of the emission window.

In this way, with the captured image calibration method of Patent Document 1, it is possible to create a calibration coefficient based on data obtained by imaging sample light having a uniform luminance distribution on the surface of the emission window, and the captured image obtained by imaging the display panel that is the inspection target can be calibrated based on the created calibration coefficient.

CITATION LIST

Patent Document

Patent Document 1: JP 2007-158577A

SUMMARY OF INVENTION

Technical Problem

Incidentally, with an integration sphere, the number of instances of the diffuse reflection in the hollow sphere body generally increases as the diameter of the sphere body increases with respect to the surface area of the emission window. If the number of instances of diffuse reflection in the integration sphere increases, the uniformity of the luminance distribution on the surface of the emission window of the sample light emitted from the integration sphere improves.

Accordingly, in the method for calibrating a captured image of a display panel disclosed in Patent Document 1 described above, the sample light with a uniform luminance distribution on the surface of the emission window can be obtained by using a large integration sphere, and an accurate calibration coefficient can be created based on the sample light.

However, due to the fact that large-sized integration spheres are generally high in cost, there is concern that if a large integration sphere is introduced only to create the calibration coefficient for calibrating the captured image as in Patent Document 1 described above, investment in equipment for image processing systems that perform detection of display unevenness in display panels will increase.

The present invention was made in view of the foregoing circumstances, and aims to provide a light-emitting apparatus that can suppress the manufacturing cost to a low level and perform light emission with high uniformity using a simple configuration, a calibration coefficient calculation method performed using the light-emitting apparatus, and a method for calibrating a captured image of an inspection target object, in which the captured image of the inspection target object is calibrated based on a calculated calibration coefficient.

Solution to Problem

According to one aspect of the present invention, a light emitting apparatus comprises: a plurality of light-emitting elements arranged at equal intervals on a circumference; and a milky white-colored emission window that is provided on a top surface portion located away from the light-emitting elements, has an outer edge smaller than the circumference on which the light-emitting elements are arranged, and allows light of the light-emitting elements to pass therethrough, wherein a radius of the circumference on which the light-emitting elements are arranged, and a separation distance between the light-emitting elements and the emission window, are set to predetermined distances.

According to this configuration, it is possible to cause light to pass through an emission window with high uniformity using a simple configuration in which multiple light-emitting elements are arranged at equal intervals on a circumference and the diameter of the circumference on which the light-emitting diodes are arranged, and the distance between the light-emitting element and the milky white-colored emission window through which the light of the light-emitting element passes, are set to predetermined distances.

With this simple configuration, the manufacturing cost of the light-emitting apparatus can be suppressed to a low level.

The light-emitting apparatus according to this aspect of the present invention, wherein a ratio between a radius of the circumference and the separation distance between the light-emitting elements and the emission window is set to be within a range of 1:1 to 1:1.5.

According to this configuration, it is possible to cause the light to pass through the emission window with optimal uniformity due to the ratio between the radius of the circumference on which the light-emitting diodes are arranged and the distance between the light-emitting element and the milky white-colored emission window through which the light of the light-emitting element passes being set to be within a range of 1:1 to 1:1.5.

The light-emitting apparatus according to this aspect of the present invention, wherein the emission window is provided with a covering material that covers an outer edge side of the emission window and blocks light emitted by the light-emitting elements on the outer edge side of the emission window.

According to this configuration, light that is incident from multiple directions on the milky white-colored emission window is diffused by the emission window, whereby the outer edge of the emission window becomes brighter than the other portions and bleeding occurs. In view of this, passage of light through the portions at which bleeding occurs is blocked due to the outer edge being covered with a covering material, and thus it is possible to hold the uniformity of the light emitted from the emission window.

A light-emitting apparatus according to another aspect of the present invention includes: a case having a bottom surface portion with a circular outer edge, a top surface portion that is symmetrical to the bottom surface portion, opposes the bottom surface portion, and has a separation distance from the bottom surface portion that is x with respect to a reference diameter when a diameter of the bottom surface portion is used as the reference diameter, and a circumferential wall portion that is formed into a cylindrical shape that is continuous between the top surface portion and the bottom surface portion; a plurality of light-emitting elements with a height distance from the bottom surface portion of the case that is set to y with respect to the reference diameter, the light-emitting elements being arranged at equal intervals on an inner circumferential surface in a circumferential direction of the circumferential wall portion; and an emission window that is provided on the top surface portion, has a diameter set to z with respect to the reference diameter, and allows the light of the light-emitting elements to pass therethrough, wherein the interior of the case is colored white.

According to this configuration, in a cylindrical case with a white-colored interior, as a ratio with respect to a reference diameter, which is the diameter of the bottom surface portion, x is set as the separation distance between the bottom surface portion and the top surface portion, y is set as the height distance from the bottom surface portion of the light-emitting elements, and z is set as the diameter of the emission window, and thus the luminance with respect to the surface of the bottom surface portion caused by the light of the light-emitting elements reflecting on the bottom surface portion of the case can be given high uniformity in a certain range.

The light-emitting apparatus according to this aspect of the present invention, wherein the separation distance is set such that its ratio with respect to the reference diameter is at least 60% or less.

The light-emitting apparatus according to this aspect of the present invention, wherein the height distance is set such that its ratio with respect to the reference diameter is at least 45% or less.

The light-emitting apparatus according to this aspect of the present invention, wherein the diameter of the emission window is set such that its ratio with respect to the reference diameter is at least 30% or less.

According to these configurations, the uniformity of the luminance with respect to the surface of the bottom surface portion can be improved by setting the separation distance between the bottom surface portion and the top surface portion to at least 60% or less, setting the height distance from the bottom surface portion of the light-emitting elements to at least 45% or less, and setting the diameter of the emission window to at least 30% or less, as ratios with respect to the reference diameter of the bottom surface portion.

The light-emitting apparatus according to the present invention, wherein the light-emitting elements are electrically connected in series.

According to this configuration, due to the fact that the light-emitting elements are electrically connected in series, it is possible to make the current supplied to the elements constant and to stabilize the light emission state. Accordingly, the light-emitting elements can be controlled easily.

The light-emitting apparatus according to the present invention, wherein the light-emitting elements are light-emitting diodes that emit red, green, and blue light.

According to this configuration, due to the fact that the light-emitting elements are constituted by light-emitting diodes that emit red, green, and blue light, it is possible to cause red light, green light, blue light, and white light, which is a combination of red, green, and blue light, to pass through the emission window.

A calibration coefficient calculation method according to the present invention comprises: a light emission step of causing the light-emitting elements of the light-emitting apparatus according to the present invention to emit light; an imaging step of positioning a lens of a camera having a solid-state image sensor at the emission window of the light-emitting apparatus and using the camera to capture a defocused image of the emission window through which sample light emitted by the light-emitting elements passes; and a calibration coefficient calculation step of calculating a calibration coefficient for calibrating sensitivity of the solid-state image sensor via the lens of the camera based on an output signal output by the solid-state image sensor when the emission window is imaged in the imaging step.

According to this configuration, a light-emitting apparatus that can be manufactured with a simple configuration at a low cost emits light, sample light with a high uniformity passes through the emission window, and the emission window is imaged out of focus. At this time, a suitable calibration coefficient can be created based on the output signal output by the solid-state image sensor.

In the calibration coefficient calculation method according to the present invention, in the imaging step, the emission window is imaged a plurality of times at a predetermined focal length of the camera.

According to this configuration, the influence of shot noise can be reduced by imaging the emission window a plurality of times at a predetermined focal length of the camera, which has the solid-state image sensor.

With a method for calibrating a captured image of an inspection target object according to the present invention, based on the calibration coefficient obtained using the above calibration coefficient calculation method, the pixels of the captured image of the inspection target object, which is formed on the solid-state image sensor due to the target object being imaged using the camera, are calibrated.

According to this configuration, the pixels of the captured image of the inspection target object can be calibrated based on the calibration coefficient suitably created using the calibration coefficient calculation method.

Advantageous Effects of Invention

According to this invention, with a simple configuration that suppresses manufacturing cost to a low level, it is possible to cause light to pass through the emission window with high uniformity and to reflect the light on the surface of the bottom surface portion with high uniformity. By using this kind of light-emitting apparatus, it is possible to obtain a suitable calibration coefficient, and by calibrating the pixels of the captured image of the inspection target object based on the calibration coefficient, it is possible to obtain a captured image of the inspection target object with no unevenness.

DESCRIPTION OF EMBODIMENTS

Next, embodiments of the present invention will be described with reference to FIGS. 1 to 13.

First Embodiment

Figure 1:
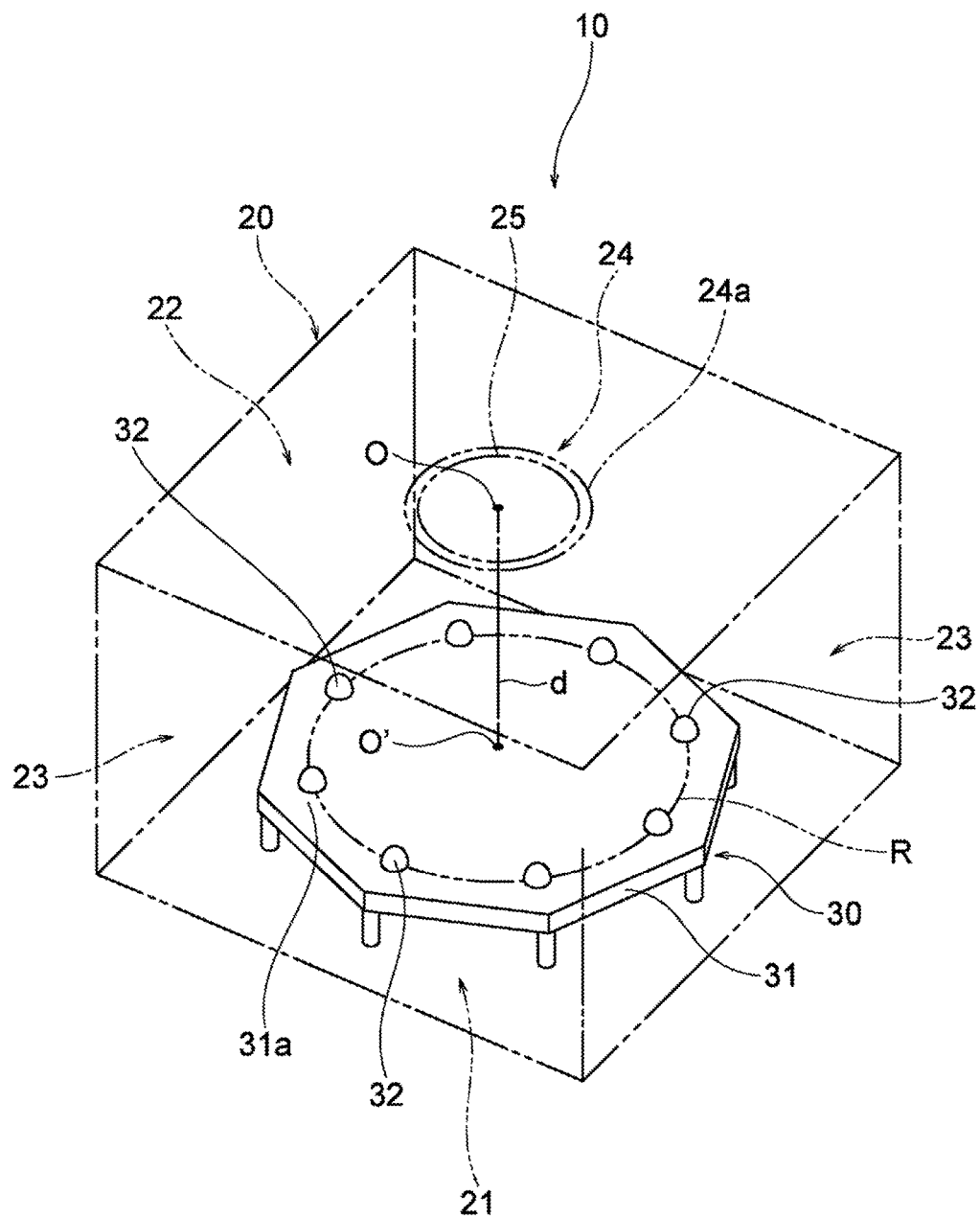
FIG. 1 is a perspective view illustrating an overview of a light-emitting apparatus according to a first embodiment of the present invention.

FIG. 1 is a perspective view illustrating an overview of a light-emitting apparatus according to a first embodiment. As shown in FIG. 1, the outer shape of a light-emitting apparatus 10 is constituted by an acrylic case 20.

In the present embodiment, the case 20 is constituted by a cubic box shape that includes a bottom surface portion 21 that is approximately rectangular in plan view, a top surface portion 22 that opposes the bottom surface portion 21 and is formed into a rectangular shape in plan view similarly to the bottom surface portion 21, and side surface portions 23 that make the bottom surface portion 21 and the top surface portion 22 continuous. The interior of the case 20 is colored white in the present embodiment.

A milky white-colored translucent emission window 24 that is circular in plan view is formed at the approximate central portion of the top surface portion 22 of the case 20. An outer edge 24a, which is the edge of the emission window 24, is provided with a black covering material 25 that has a certain width from the outer edge 24a in the inner circumferential direction of the emission window 24 and covers the outer edge 24a along the circumference of the emission window 24.

A light-emitting portion 30 is provided on the bottom surface portion 21 in the case 20. In this embodiment, the light-emitting portion 30 includes a platform 31 that is approximately octagonal in plan view. A virtual circle R that is coaxial with the emission window 24, which is formed on the top surface portion 22 and is approximately circular in plan view, is provided on an upper surface 31a of the platform 31.

Multiple (in the present embodiment, eight) light-emitting diodes 32, which are light-emitting elements, are arranged at equal intervals on a circumference equal to that of the virtual circle R. In the present embodiment, light-emitting diodes that emit three colors of light, namely red (R), green (G), and blue (B), are used for the light-emitting diodes 32.

In the present embodiment, between light-emitting diodes 32, red (R) terminals are electrically connected in series to each other, green (G) terminals are electrically connected in series to each other, and blue (B) terminals are electrically connected in series to each other.

Figure 2:
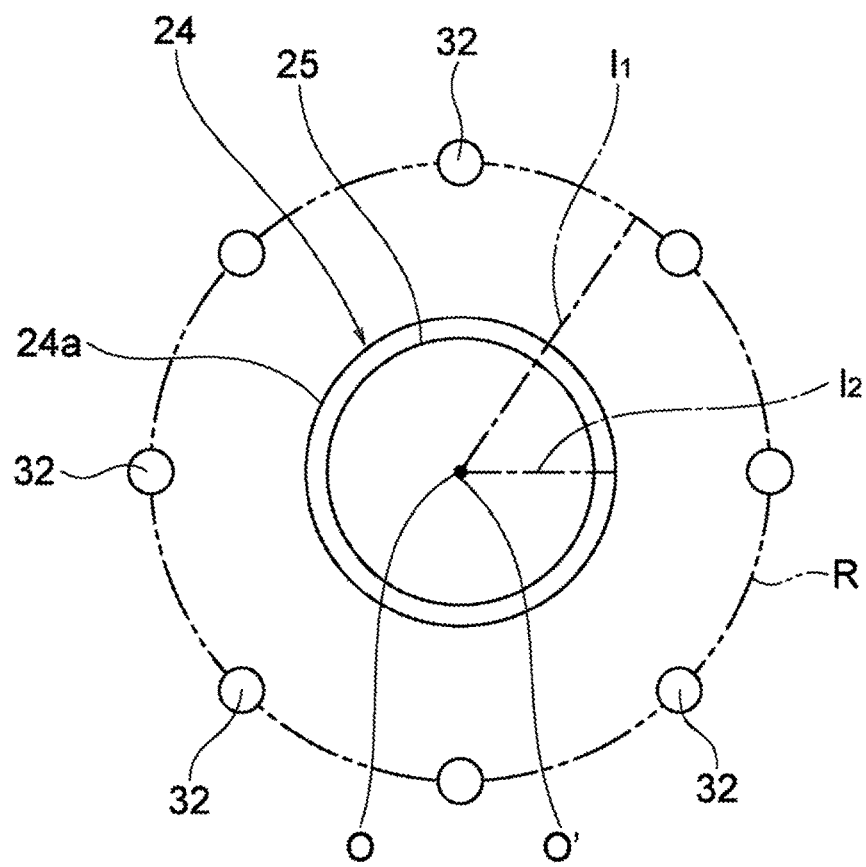
FIG. 2 similarly schematically shows an arrangement configuration of a light-emitting portion and an emission window according to the embodiment.
Figure 3:
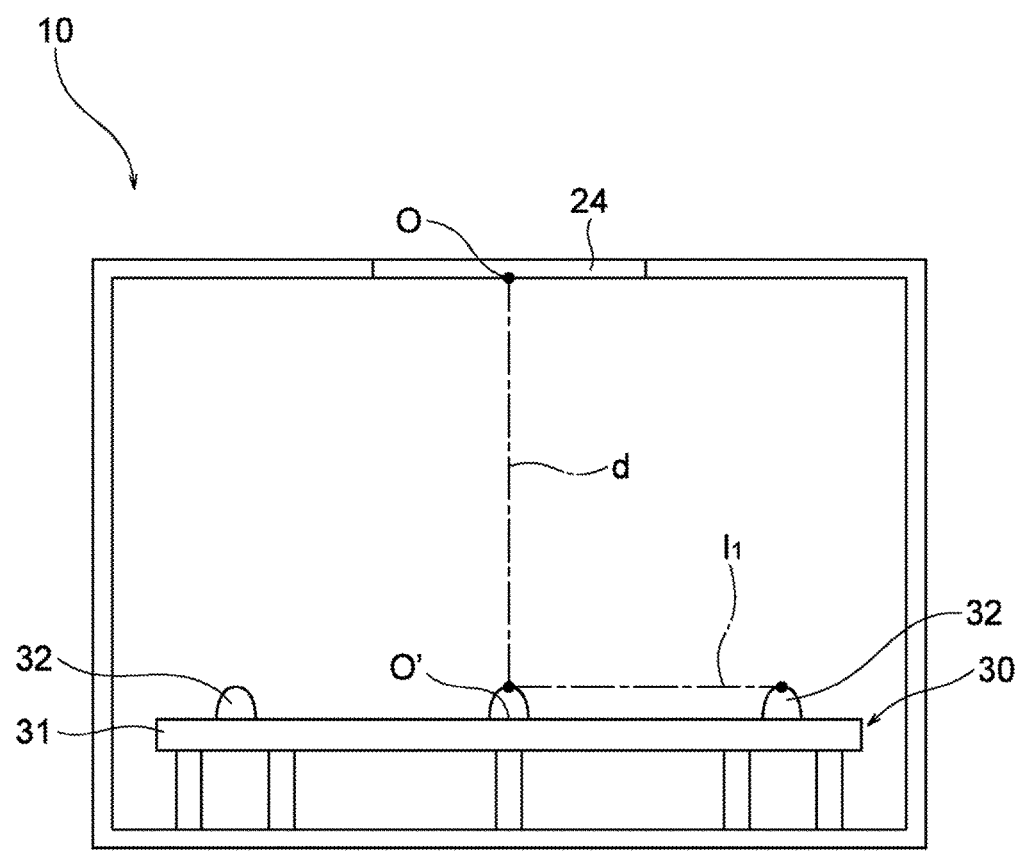
FIG. 3 similarly schematically shows an arrangement configuration of a light-emitting portion and an emission window according to the embodiment.

FIGS. 2 and 3 are diagrams schematically showing an arrangement configuration of the light-emitting portions 30 and the emission window 24. As shown in FIG. 2, the emission window 24 is formed on the top surface portion 22 such that a central point O thereof is arranged at a central point O' of a virtual circle R set in the light-emitting portion 30, or in other words, so as to be concentric with the virtual circle R.

The outer edge 24a of the emission window 24 is formed so as to be smaller than the circumference of the virtual circle R set in the light-emitting portion 30. Specifically, in the present embodiment, a radius $I_1$ of the virtual circle R is set to be 10 cm, and a radius 12 of the emission window 24 is set to be 5 cm.

On the other hand, as shown in FIG. 3, the ratio between the radius $I_1$ of the virtual circle R on which the light-emitting diodes 32 are arranged, and which is set in the light-emitting portion 30, and a distance d between the central point O of the emission window 24 and the central point O' of the virtual circle R is set to be 1:1.2 in the present embodiment, as will be described later. Therefore, the distance d between the central point O of the emission window 24 and the central point O' of the virtual circle R is set to be 12 cm.

The luminance at the radius $I_1$ of the virtual circle R caused by emission of light by the light emission portion 30 is influenced by the ratio between the radius $I_1$ of the virtual circle R and the distance d between the central point O of the emission window 24 and the central point O' of the virtual circle R.

FIGS. 4 and 5 schematically show theoretical effects on the uniformity of the luminance with respect to the emission window caused by the ratio between the radius of the virtual circle and the distance between the central point of the emission window and the central point of the virtual circle according to the present embodiment.

Figure 4A:
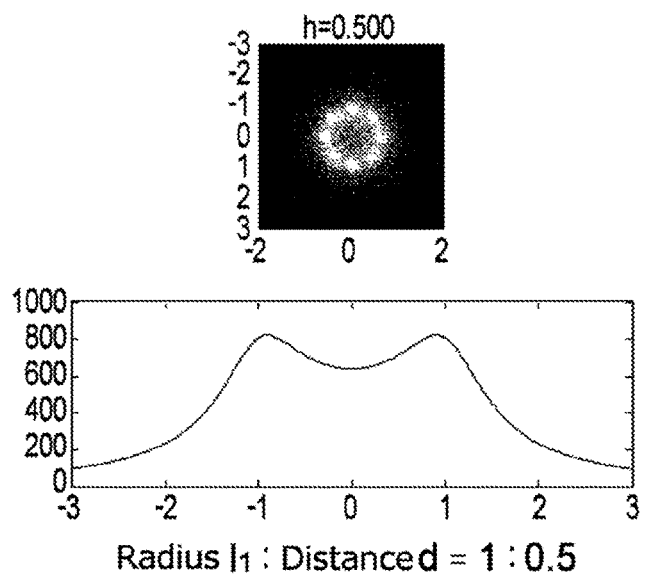
FIG. 4 similarly schematically shows a theoretical effect on uniformity of luminance with respect to the emission window caused by the ratio between the radius of a virtual circle and a distance between a central point of the emission window and the central point of the virtual circle according to the embodiment.

As shown in FIG. 4(a), in the case where 1:0.5 is used as the ratio between the radius $I_1$ of the virtual circle R and the distance d between the central point O of the emission window 24 and the central point O' of the virtual circle R, the eight light-emitting diodes 32 will perform point light emission at the positions at which they are arranged, and the gaps between adjacent light-emitting diodes 32 will be joined due to the light emission performed by the light-emitting diodes 32, resulting in a state in which light is emitted in the form of a ring.

Specifically, according to a graph composed of a horizontal axis schematically showing the size of the radius $I_1$ of the virtual circle R and a vertical axis schematically showing the luminances of the light-emitting diodes 32, the luminance reaches its maximum at the positions at which the radius $I_1$, which is the peripheral portion of the virtual circle R, is 1 and −1, and there is a significant difference between the luminances at those positions and the luminance at the position at which the radius $I_1$ is 0, or in other words, the position of the central point O' of the virtual circle R.

Figure 4B:
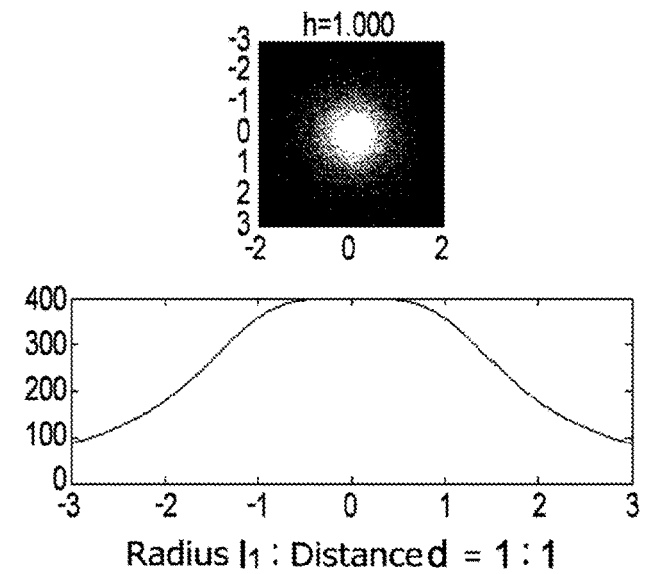

As shown in FIG. 4(b), in the case where 1:1 is used as the ratio between the radius $I_1$ of the virtual circle R and the distance d between the central point O of the emission window 24 and the central point O' of the virtual circle R, the eight light-emitting diodes 32 emit light, resulting in a state in which all of the light-emitting diodes 32 join together due to light emission and perform a planar light emission.

Specifically, according to a graph composed of a horizontal axis that schematically shows the size of the radius $I_1$ of the virtual circle R and a vertical axis that schematically shows the luminance of the light-emitting diodes 32, the luminance reaches its maximum at the position at which the radius $I_1$ is 0 to 0.5 and 0 to −0.5, which is the central portion of the virtual circle R, and no difference occurs between the luminance at that position and the luminance at the positions at which the radius $I_1$ is 1 and −1, which are the peripheral portion of the virtual circle R.

Thus, in the case where 1:0.5 is used as the ratio between the radius $I_1$ of the virtual circle R and the distance d between the central point O of the emission window 24 and the central point O' of the virtual circle R, a difference occurs between the luminances at the central portion and the peripheral portion of the virtual circle R. On the other hand, in the case where 1:1 is used as the ratio between the radius $I_1$ of the virtual circle R and the distance d between the central point O of the emission window 24 and the central point O' of the virtual circle R, almost no difference occurs between the luminances at the central portion and the peripheral portion of the virtual circle R.

Figure 5A:
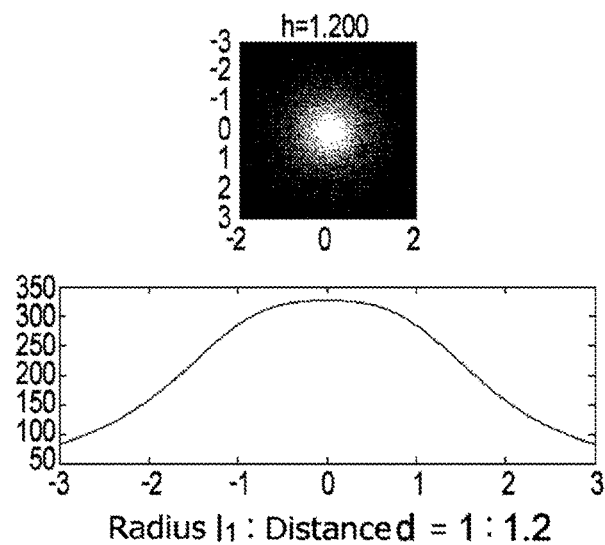
FIG. 5 similarly schematically shows an effect on uniformity of luminance with respect to the emission window caused by the ratio between the radius of a virtual circle and a distance between the central point of the emission window and the central point of the virtual circle according to the embodiment.

On the other hand, as shown in FIG. 5(a), in the case where 1:1.2 is used as the ratio between the radius $I_1$ of the virtual circle R and the distance d between the central point O of the emission window 24 and the central point O' of the virtual circle R, all of the light-emitting diodes 32 join together due to light emission and perform the planar light emission, similarly to the case described above.

Specifically, according to the graph composed of a horizontal axis schematically showing the size of the radius $I_1$ of the virtual circle R and a vertical axis schematically showing the luminance of the light-emitting diodes 32, the luminance reaches its maximum at the position at which the radius $I_1$ is 0, or in other words, the position of the central point O' of the virtual circle R, and no significant difference occurs between the luminance at that position and the luminances at the positions at which the radius $I_1$ is 1 and −1, which are the peripheral portion of the virtual circle R.

Figure 5B:
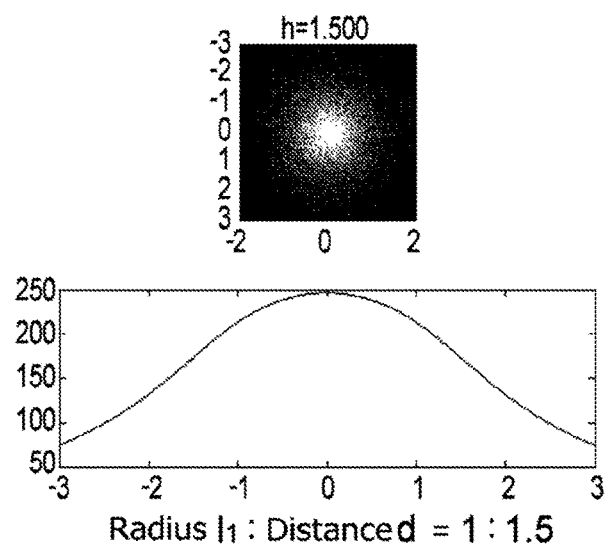

As shown in FIG. 5(b), in the case where 1:1.5 is used as the ratio between the radius $I_1$ of the virtual circle R and the distance d between the central point O of the emission window 24 and the central point O' of the virtual circle R, all of the light-emitting diodes 32 join together due to light emission and perform the planar light emission, similarly to the case described above.

Specifically, according to the graph composed of a horizontal axis schematically showing the size of the radius $I_1$ of the virtual circle R and a vertical axis schematically showing the luminance of the light-emitting diodes 32, the luminance reaches its maximum at the position of the central point O' of the virtual circle R, at which the radius $I_1$ is 0, and no significant difference occurs between the luminance at that position and the luminances at the positions at which the radius $I_1$ is 1 and −1, which are the peripheral portion of the virtual circle R.

Thus, in the case where 1:1.2 is used as the ratio between the radius $I_1$ of the virtual circle R and the distance d between the central point O of the emission window 24 and the central point O' of the virtual circle R, and in the case where 1:1.5 is used as the ratio between the radius $I_1$ of the virtual circle R and the distance d between the central point O of the emission window 24 and the central point O' of the virtual circle R, no significant difference occurs between the luminances at the central portion and the peripheral portion of the virtual circle R.

Incidentally, in the case where 1:1.2 or 1:1.5 is used as the ratio between the radius $I_1$ of the virtual circle R and the distance d between the central point O of the emission window 24 and the central point O' of the virtual circle R, the surface area of the virtual circle R in which the luminance is at its maximum is smaller in comparison to that in the case where 1:1 is used as the ratio between the radius $I_1$ of the virtual circle R and the distance d between the central point O of the emission window 24 and the central point O' of the virtual circle R.

Accordingly, theoretically, if 1:1 is used as the ratio between the radius $I_1$ of the virtual circle R and the distance d between the central point O of the emission window 24 and the central point O' of the virtual circle R, it is possible to obtain a surface area with a size at which the light that passes through the emission window 24 is uniform with respect to the plane of the emission window 24 and is easy to see.

FIG. 6 is a diagram schematically showing results of observing the influence on the uniformity of the luminance with respect to the plane of the emission window, based on an experiment in which the ratio between the radius of the virtual circle and the distance between the central point of the emission window and the central point of the virtual circle according to the present embodiment is changed.

Figure 6A:
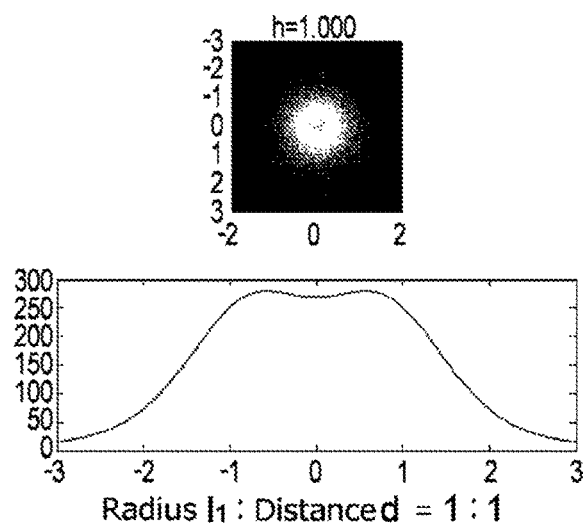
FIG. 6 similarly schematically shows a result of observing the effect on uniformity of luminance with respect to the emission window based on an experiment in which the ratio between the radius of a virtual circle and a distance between the central point of the emission window and the central point of the virtual circle according to an embodiment is changed.

As shown in FIG. 6(a), in the case where 1:1 is used as the ratio between the radius $I_1$ of the virtual circle R and the distance d between the central point O of the emission window 24 and the central point O' of the virtual circle R, the eight light-emitting diodes 32 emit light, resulting in a state in which all of the light-emitting diodes 32 join together due to light emission, the portion of the central point O' of the virtual circle R is slightly darker, and light is emitted in the form of a ring.

Specifically, according to the graph composed of a horizontal axis schematically showing the size of the radius $I_1$ of the virtual circle R and a vertical axis schematically showing the luminance of the light-emitting diodes 32, a difference occurs between the luminance at the position of the central point O' of the virtual circle R, at which the radius $I_1$ is 0, and the luminances at the positions at which the radius $I_1$ is near 1 and near −1, which are the peripheral portion of the virtual circle R.

Figure 6B:
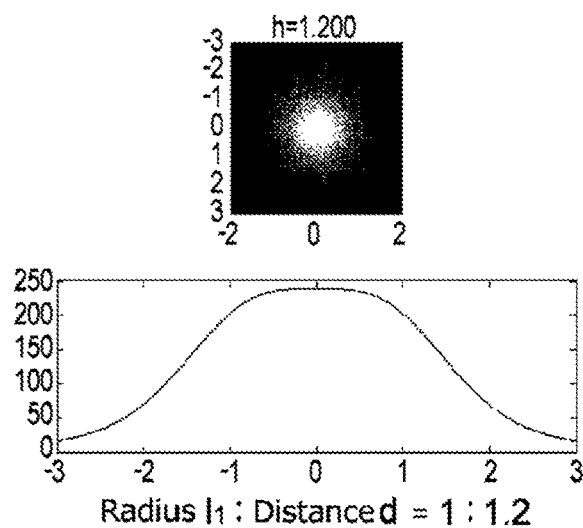

As shown in FIG. 6(b), in the case where 1:1.2 is used as the ratio between the radius $I_1$ of the virtual circle R and the distance d between the central point O of the emission window 24 and the central point O' of the virtual circle R, the eight light-emitting diodes 32 emit light, resulting in a state in which all of the light-emitting diodes 32 join together due to light emission and perform the planar light emission.

Specifically, according to a graph composed of a horizontal axis that schematically shows the size of the radius $I_1$ of the virtual circle R and a vertical axis that schematically shows the luminance of the light-emitting diodes 32, the luminance reaches its maximum at the positions at which the radius $I_1$ is about 0 to 0.5 and 0 to −0.5, which is the central portion of the virtual circle R, and no significant difference occurs between the luminance at that position and the luminances at the positions at which the radius $I_1$ is 1 and −1, which are the peripheral portion of the virtual circle R.

Figure 6C:
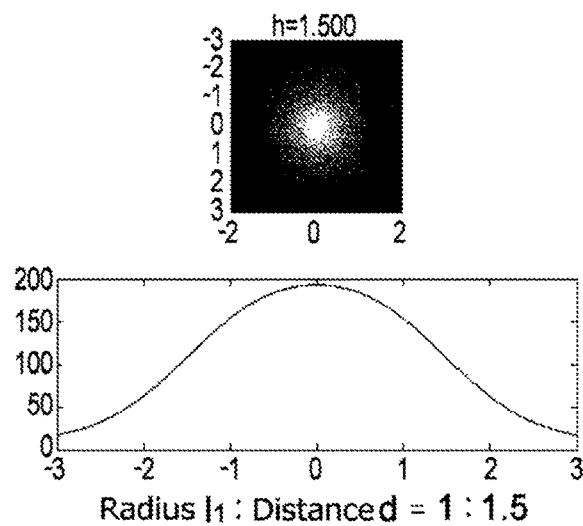

As shown in FIG. 6(c), in the case where 1:1.5 is used as the ratio between the radius $I_1$ of the virtual circle R and the distance d between the central point O of the emission window 24 and the central point O' of the virtual circle R, the eight light-emitting diodes 32 emit light, resulting in a state in which all of the light-emitting diodes 32 join together due to emitting light and perform the planar light emission.

Specifically, according to a graph composed of a horizontal axis that schematically shows the size of the radius $I_1$ of the virtual circle R and a vertical axis that schematically shows the luminance of the light-emitting diodes 32, the luminance reaches its maximum at the positions at which the radius $I_1$ is about 0 to 0.3 and 0 to −0.3, which is the central portion of the virtual circle R, and no significant difference occurs between the luminance at that position and the luminances at the positions at which the radius $I_1$ is 1 and −1, which are the peripheral portion of the virtual circle R.

Thus, in the case where 1:1.2 is used as the ratio between the radius $I_1$ of the virtual circle R and the distance d between the central point O of the emission window 24 and the central point O' of the virtual circle R, and in the case where 1:1.5 is used as the ratio between the radius $I_1$ of the virtual circle R and the distance d between the central point O of the emission window 24 and the central point O' of the virtual circle R, no significant difference occurs between the luminances at the central portion and the peripheral portion of the virtual circle R.

Incidentally, in the case where 1:1.2 or 1:1.5 is used as the ratio between the radius $I_1$ of the virtual circle R and the distance d between the central point O of the emission window 24 and the central point O' of the virtual circle R, the surface area of the virtual circle R in which the luminance is at its maximum is larger in comparison to that in the case where 1:1.2 is used as the ratio between the radius $I_1$ of the virtual circle R and the distance d between the central point O of the emission window 24 and the central point O' of the virtual circle R.

Thus, in the experiment, if 1:1.2 is used as the ratio between the radius $I_1$ of the virtual circle R and the distance d between the central point O of the emission window 24 and the central point O' of the virtual circle R, it is possible to obtain a surface area with a size at which the light that passes through the emission window 24 is uniform with respect to the plane of the emission window 24 and is easy to see.

Accordingly, in the present embodiment, setting is performed such that the radius $I_1$ of the virtual circle R set in the light-emitting portion 30 is 10 cm and the distance d between the central point O of the emission window 24 and the central point O' of the virtual circle R is 12 cm, or in other words, setting is performed such that the ratio between the radius $I_1$ of the virtual circle R and the distance d between the central point O of the emission window 24 and the central point O' of the virtual circle R is 1:1.2.

Incidentally, it is theoretically preferable to use 1:1 as the ratio between the radius $I_1$ of the virtual circle R and the distance d between the central point O of the emission window 24 and the central point O' of the virtual circle R, from the viewpoint of making the light that passes through the emission window 24 uniform on the surface of the emission window 24. However, in the experiment, due to using 1:1.2 as the ratio, the light passing through the emission window 24 was uniform on the surface of the emission window 24.

Thus, although various reasons, such as the shape of the case 20 and the reflection state in the case 20, are conceivable as reasons why the theoretical value and the experimental value differ, it is thought that there is a large dependency on the light distribution properties of the light-emitting diodes that are used.

In the present embodiment, a light-emitting diode is used which has a light distribution property in which light that passes through the emission window 24 is made uniform with respect to the surface of the emission window 24 by using 1:1.2 as the ratio between the radius $I_1$ of the virtual circle R and the distance d between the central point O of the emission window 24 and the central point O' of the virtual circle R under the condition of using a cubic box-shaped case 20 with a white-colored interior.

Of course, there is no limitation to the light distribution property of the light-emitting diodes used in the present embodiment, and various light-emitting diodes can be used as long as the light that passes through the emission window 24 is uniform with respect to the surface of the emission window 24.

In particular, when the ratio between the radius $I_1$ of the virtual circle R and the distance d between the central point O of the emission window 24 and the central point O' of the virtual circle R is within the range of 1:1 to 1:1.5, it is preferable to use a light-emitting diode that has the light distribution property in which the light that passes through the emission window 24 is uniform with respect to the surface of the emission window 24.

Due to using 1:1.2 as the ratio between the radius $I_1$ of the virtual circle R and the distance d between the central point O of the emission window 24 and the central point O' of the virtual circle R, with the light emission of the light-emitting diodes 32 of the light-emitting portion 30 of the light-emitting apparatus 10 with the above-described configuration, a significant difference no longer occurs between the luminances at the central portion and the peripheral portion of the virtual circle R.

In particular, in the present embodiment, the radius $I_1$ of the virtual circle R is set to be 10 cm, the radius 12 of the emission window 24 is set to be 5 cm, and the outer edge 24a of the emission window 24 is formed so as to be smaller than the circumference of the virtual circle R set in the light emission portion 30, and therefore the light at and near the position of the central point O' of the virtual circle R, at which the luminance is at its maximum, passes through the emission window 24.

Accordingly, when the light in this range passes through the emission window 24, the uniformity of the luminance with respect to the surface of the emission window 24 is high.

Moreover, in the present embodiment, the emission window 24 is translucent and milky white, and therefore when the light passes through the emission window 24, the light diffuses in the range of the surface of the emission window 24, and the luminance with respect to the surface of the emission window 24 can more effectively be made uniform.

Furthermore, due to light that is incident from many directions being diffused by the emission window 24, the outer edge 24a of the emission window 24 becomes brighter and bleeds more in comparison to the other portions of the emission window 24, but in the present embodiment, due to the fact that the outer edge 24a is covered with a black covering material 25, the passage of light from the outer edge 24a side is blocked, and the uniformity of the emitted light from the emission window 24 can be held.

In the present embodiment, between light-emitting diodes 32, the red (R) terminals are electrically connected in series to each other, the green (G) terminals are electrically connected in series to each other, and the blue (B) terminals are electrically connected in series to each other, and therefore the light emission state of the eight light-emitting diodes 32 can be stabilized with a constant current supplied to the light-emitting diodes 32. Accordingly, the light-emitting diodes 32 can be controlled easily.

On the other hand, due to the fact that the inner portion of the case 20 is colored white in the present embodiment, the light is reflected and diffused by the interior portion of the case 20 when the light-emitting diodes 32 emit light, and the light that passes through the emission window 24 can be favorably made uniform.

This type of light-emitting apparatus 10 is used in an application of creating a calibration coefficient for calibrating variations in sensitivity or the like according to the unique properties of individual cameras caused by sensitivity variations in a solid-state image sensor.

Second Embodiment

Next, a second embodiment of the present invention will be described with reference to FIGS. 7 to 9. Note that in FIGS. 7 to 9, configurations similar to those of the first embodiment are denoted by the same reference signs and detailed description thereof is not included here.

Figure 7:
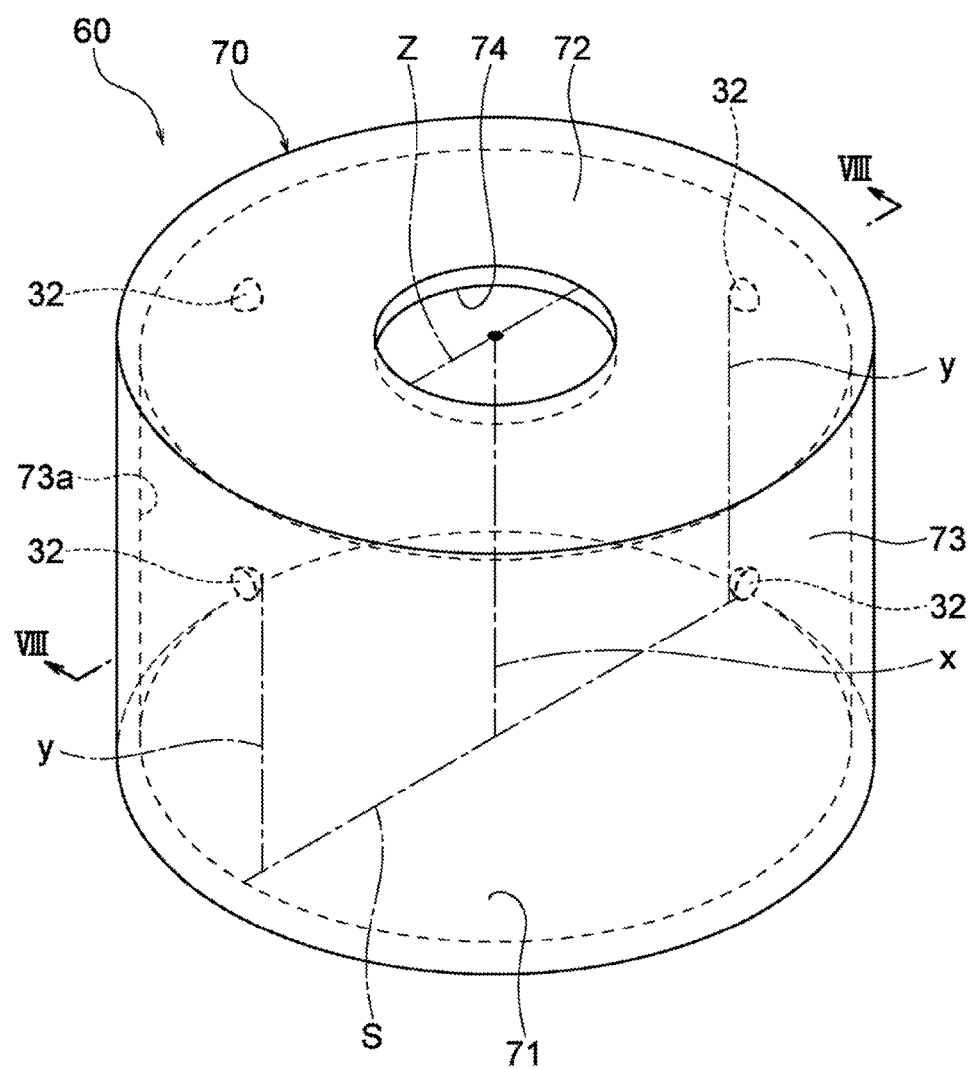
FIG. 7 is a perspective view illustrating an overview of a light-emitting apparatus according to a second embodiment of the present invention.

FIG. 7 is a perspective view illustrating an overview of a light-emitting apparatus according to the second embodiment. As shown in FIG. 7, the outer shape of a light-emitting apparatus 60 is constituted by an acrylic case 70.

In the present embodiment, the case 70 is formed into a cylindrical shape having a bottom surface portion 71 that is circular in plan view and has a circular outer edge, a top surface portion 72 that is circular in plan view, is symmetrical with the bottom surface portion 71, and opposes the bottom surface portion 71, and a cylindrical circumferential wall portion 73 that is continuous between the top surface portion 72 and the bottom surface portion 71.

Multiple (in the present embodiment, four) light-emitting diodes 32, which are light-emitting elements, are arranged at equal intervals on an inner circumferential surface 73a in the circumferential direction of the circumferential wall portion 73 of the case 70.

On the other hand, an emission window 74 cut out in a shape that is circular in plan view is formed at the approximate central portion of the top surface portion 72 of the case 70.

Figure 8:
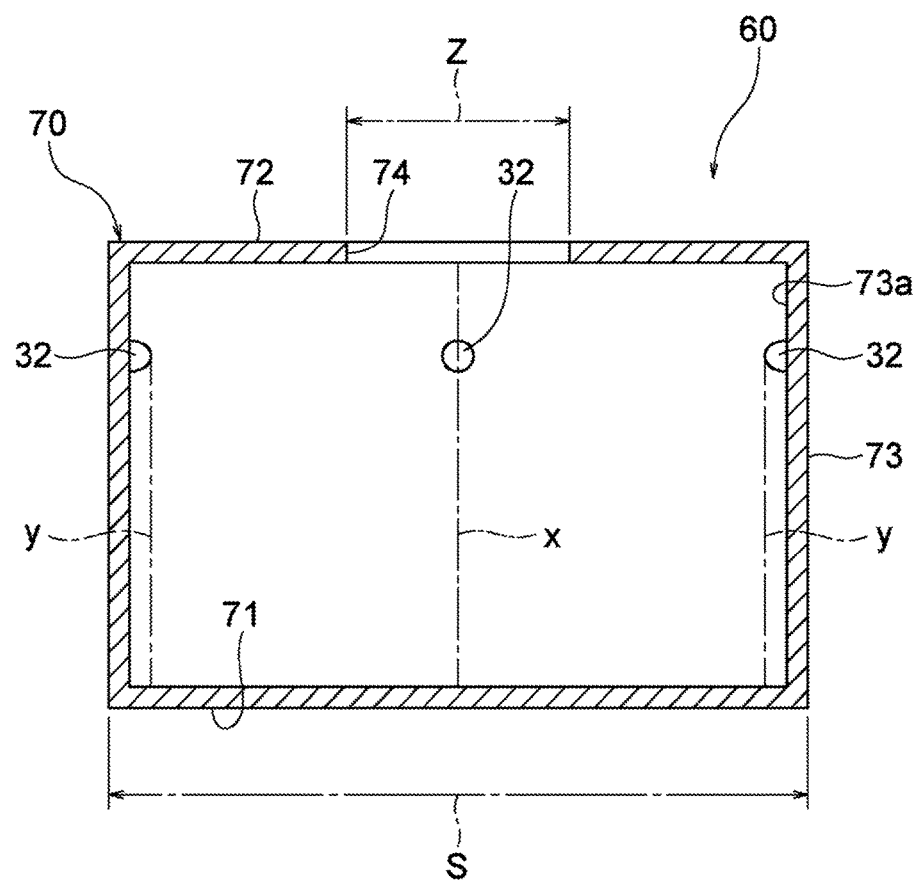
FIG. 8 is a cross-sectional view taken along line VIII-VIII in FIG. 7.

FIG. 8 is a cross-sectional view taken along line VIII-VIII in FIG. 7. As shown in FIG. 8, in the present embodiment, the diameter of the bottom surface portion 71 of the light-emitting apparatus 60 is set to be a reference diameter S.

The separation distance between the bottom surface portion 71 and the top surface portion 72 opposing the bottom surface portion 71 is set to be x according to the ratio with respect to the reference diameter S. In the present embodiment, if 1.0 is used as the reference diameter S, x is set to be 0.575, which is 60% or less of the reference diameter S.

On the other hand, the height distance from the bottom surface portion 71 of the light-emitting diodes 32 arranged on the inner circumferential surface 73a in the circumferential direction of the circumferential wall portion 73 is set to be y according to the ratio with respect to the reference diameter S. In the present embodiment, if 1.0 is used as the reference diameter S, y is set to be 0.4325, which is 45% or less of the reference diameter S.

The diameter of the emission window 74, which is circular in plan view and is formed at approximately the central portion of the top surface portion 72, is set to be z according to the ratio with respect to the reference diameter S. In the present embodiment, if 1.0 is used as the reference diameter S, z is set to be 0.29, which is 30% or less of the reference diameter S.

In the present embodiment, the inner portion of the case 70 having the above-described configuration is colored a matte white color with a reflectance that is set to 0.96%.

Thus, in the case where the reference diameter S is used as the diameter of the bottom surface portion 71, the ratio between the reference diameter S and the dimensions of the portions of the case 70 are set as described above, and thereby the luminance with respect to the surface of the bottom surface portion 71, which is achieved due to the light of the light-emitting diodes 32 being reflected by the bottom surface portion 71, is approximately uniform in a certain range.

Figure 9:
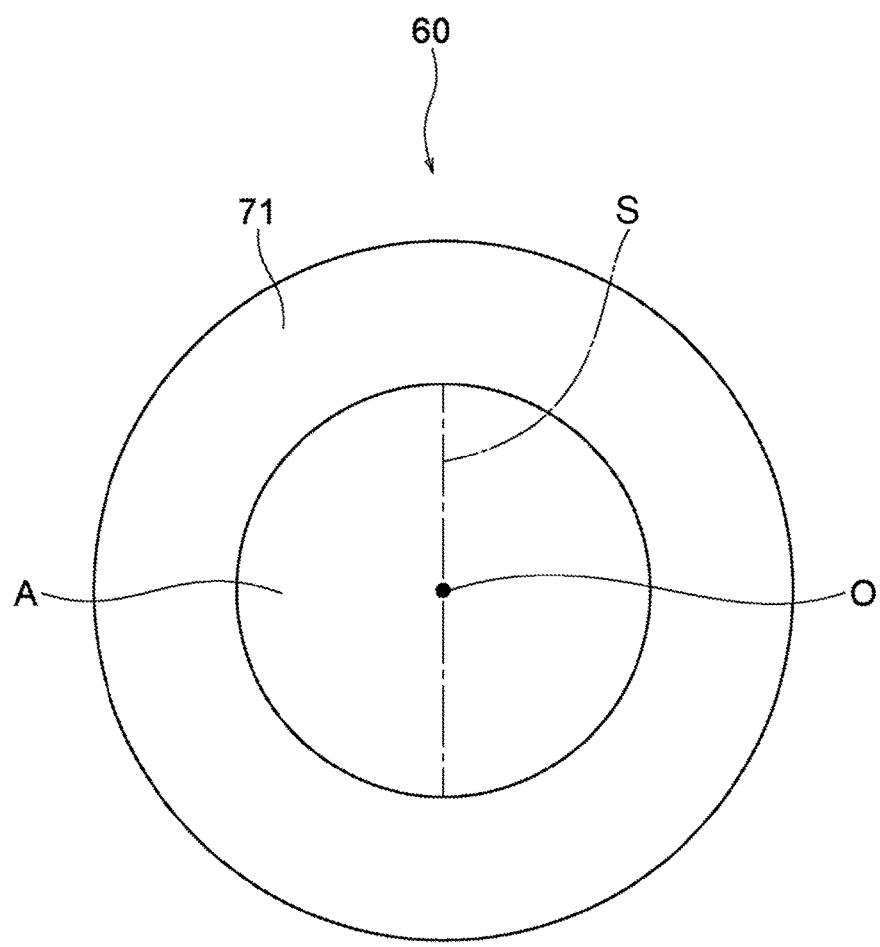
FIG. 9 is similarly a schematic diagram illustrating an overview of a state of luminance of a light-emitting apparatus according to an embodiment.

Specifically, as shown in FIG. 9, which illustrates an overall state of the luminance achieved by the light-emitting apparatus 60 according to the present embodiment, if the ratios between the reference diameter S and the dimensions of the portions of the case 70 are set as described above, the luminance achieved by the light-emitting apparatus 60 is uniform within the range (there is an error of ±0.2% in this range) of surface area A of the rotational path formed by rotating the diameter s, which has a ratio of 0.55 with respect to the reference diameter S, using the central point O of the bottom surface portion 71 as the rotation center.

Thus, in the cylindrical case 70 of the light-emitting apparatus 60 of the present embodiment, according to the ratio with respect to the reference diameter S in the case of using 1.0 as the reference diameter S, which is the diameter of the bottom surface portion 71, 0.575 (=x) is used as the separation distance between the bottom surface portion 71 and the top surface portion 72, 0.4325 (=y) is used as the height distance from the bottom surface portion 71 of the light-emitting diode 32, and 0.29 (=z) is used as the diameter of the emission window 74. The interior portion of the case 70 is colored with a matte white color having a reflectance that is set to 0.96%.

In this case, the luminance with respect to the surface of the bottom surface portion 71 achieved due to the light of the light-emitting diodes 32 being reflected by the bottom surface portion 71 of the case 70 can be made approximately uniform in a certain range.

This type of light-emitting apparatus 60 is used in an application of creating a calibration coefficient for calibrating variations in sensitivity or the like according to the unique properties of individual cameras caused by sensitivity variations in a solid-state image sensor.

Method for Creating Calibration Coefficient

Next, a method for creating a calibration coefficient will be described with reference to the light-emitting apparatus 10 (60) according to the first embodiment and the second embodiment.

Figure 10:
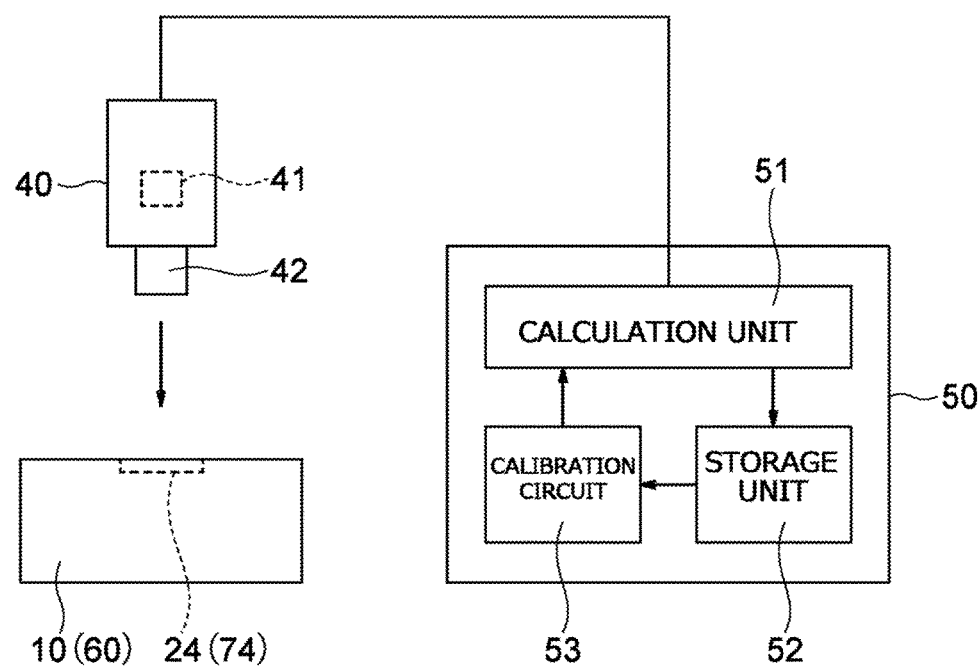
FIG. 10 is a diagram illustrating an overview of a method for creating a calibration coefficient for calibrating variations in the sensitivity of a camera or the like using the light-emitting apparatus according to the first embodiment and the second embodiment.

FIGS. 10 to 13 are diagrams illustrating an overview of a method for creating a calibration coefficient for calibrating variations in the sensitivity of a solid-state image sensor of a camera using the light-emitting apparatus 10 (60) according to the first embodiment and the second embodiment. As shown in FIG. 10, a camera 40 includes a solid-state image sensor 41 and a lens 42, and is connected to a calibration apparatus 50.

Figure 11:
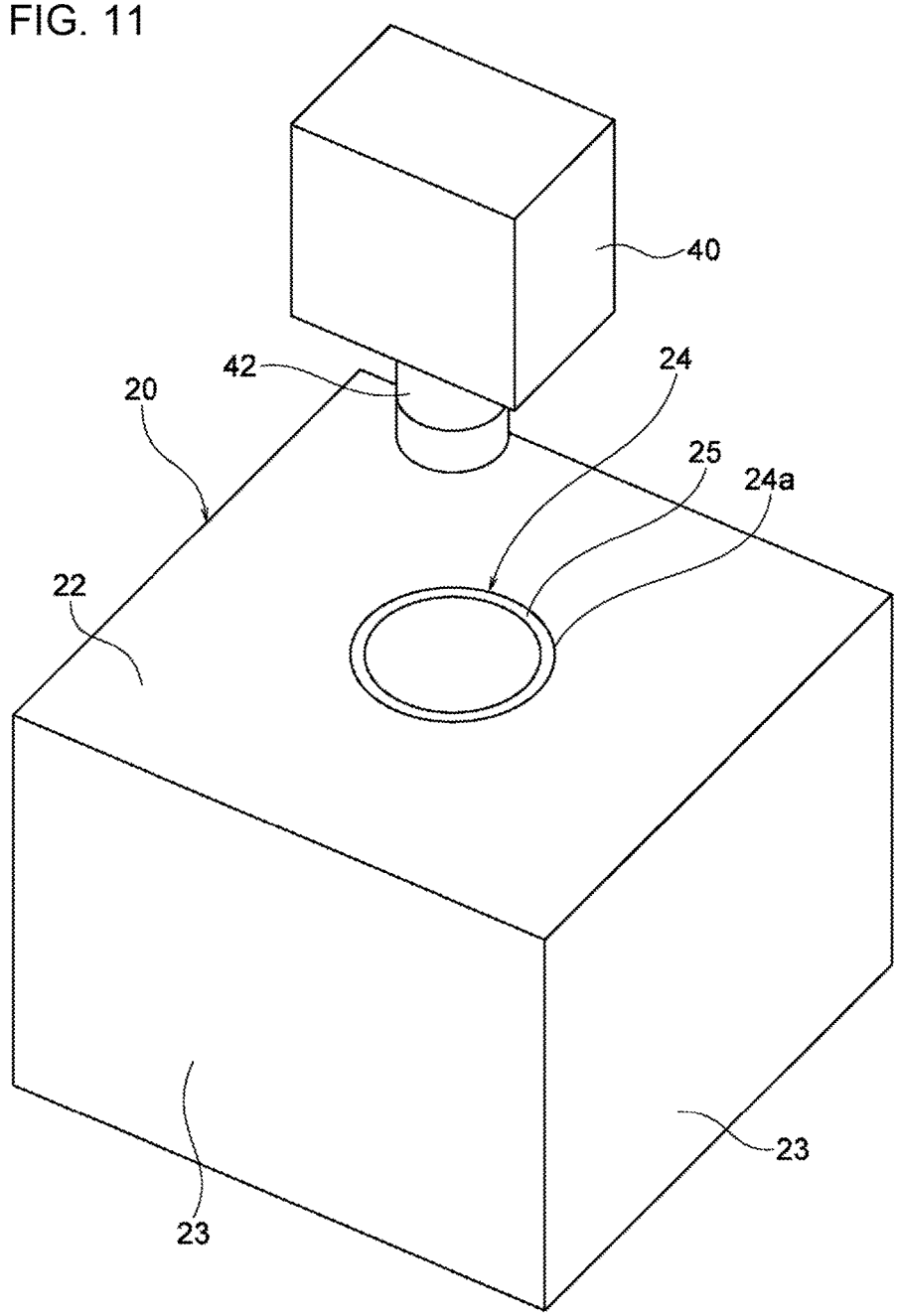
FIG. 11 is similarly a diagram illustrating an overview of a method for creating a calibration coefficient for calibrating variation in the sensitivity of a camera or the like using the light-emitting apparatus.

In the case of using the light-emitting apparatus 10 according to the first embodiment, as shown in FIGS. 10 and 11, the lens 42 of the camera 40 is positioned at the emission window 24 of the light-emitting apparatus 10, and imaging is performed on the emission window 24, through which sample light, which is light emitted by the light-emitting diodes 32 of the light-emitting portion 30, passes.

Figure 12:
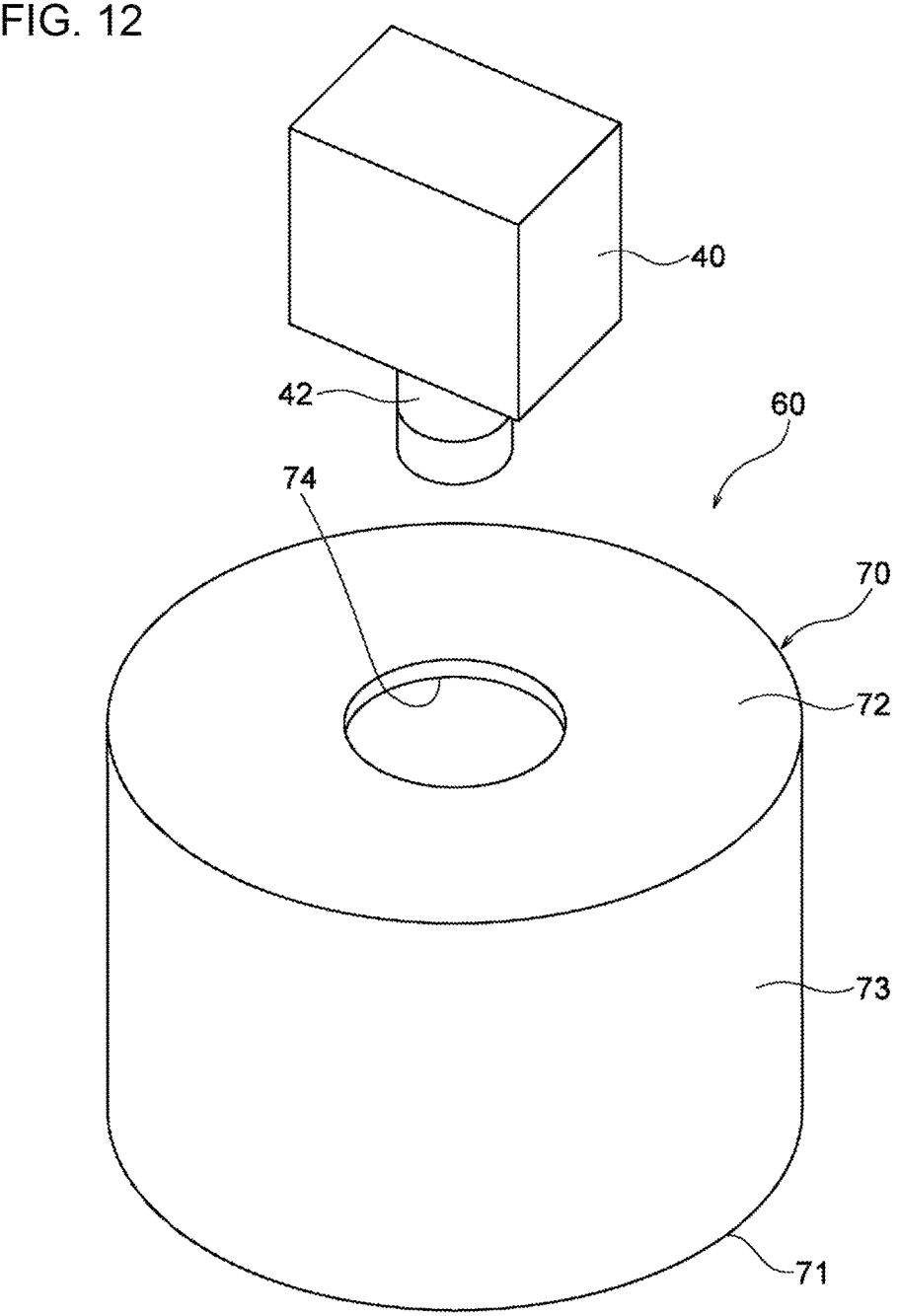
FIG. 12 is similarly a diagram illustrating an overview of a method for creating a calibration coefficient for calibrating variation in the sensitivity of a camera or the like using the light-emitting apparatus.

On the other hand, in the case of using the light-emitting apparatus 60 according to the second embodiment, as shown in FIGS. 10 and 12, the lens 42 of the camera 40 is positioned at the emission window 74 of the light-emitting apparatus 60, and imaging is performed via the emission window 74 on the surface on which the sample light, which is light emitted by the light-emitting diodes 32, is reflected on the bottom surface portion 71 of the case 70.

Figure 13:
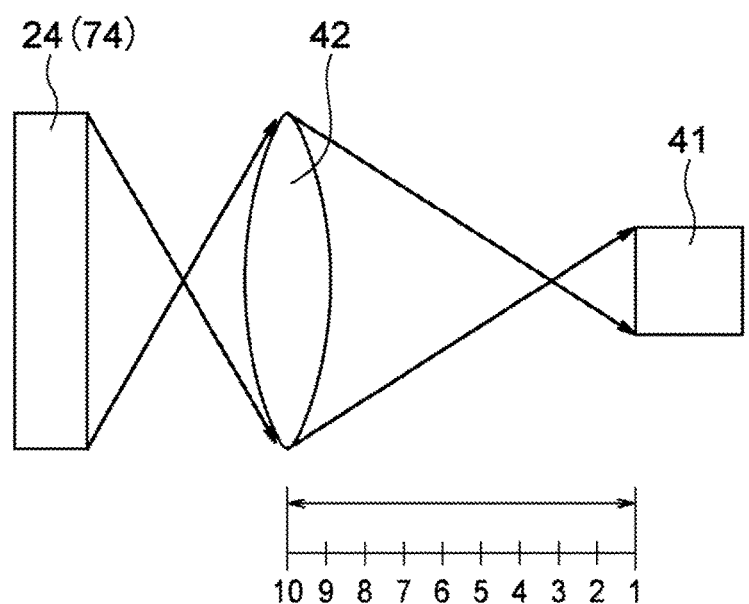
FIG. 13 is similarly a diagram illustrating an overview of a method for creating a calibration coefficient for calibrating variations in the sensitivity of a camera or the like using the light-emitting apparatus.

At this time, as shown in FIG. 13, in the present embodiment, the focal length is changed over 10 stages due to the lens 42 moving toward and away from the solid-state image sensor 41, and the emission window 24 (74) through which the sample light passes is imaged at each of the focal lengths at the ten stages.

As shown once again in FIG. 10, a program stored in a calculation unit 51 built into the calibration apparatus 50 creates the calibration coefficient based on the captured image data obtained by imaging the sample light. In the creation of the calibration coefficient, first, the emission window 24 (74) through which the sample light passes is imaged at each focal distance in a state in which the light-emitting diodes 32 emit red (R) light, for example.

At this time, at each focal length, the lens 42 is brought close to the emission window 24 (74) of the light-emitting apparatus 10, is put in a so-called defocused state of being out-of-focus, and in this state, the emission window 24 (74) through which the sample light passes is imaged.

The imaging of the emission window 24 (74) through which the sample light passes is performed multiple times at a predetermined focal length (e.g., the focal length at the fifth stage) from the viewpoint of reducing the influence of the shot noise.

In the multiple instances of imaging the emission window 24 (74) through which the sample light passes, an output signal from the solid-state image sensor 41, which has sensitivity variations, is normalized such that the average value thereof is 1, and the inverse of the normalized average value is calculated as the calibration coefficient.

Procedures similar to these are executed repeatedly for green (G) and blue (B) as well, whereby calibration coefficients for red (R), green (G), and blue (B) are created. The created calibration coefficients are stored in a storage unit 52.

For each of the colors red (R), green (G), and blue (B), which are the three primary colors of light, the number of coefficients needed is a number obtained by multiplying the total number of elements in the solid-state image sensor 41 by the number of focal lengths.

In other words, the number of calibration coefficients that are required is:

total number of elements in solid-state image sensor×number of focal lengths×3(R,G,B)

For example, if the solid-state image sensor 41 is 29M and there are 10 focal lengths, this is calculated for each of R, G, and B, and the results of the calculations are converted into a floating-point format (4 bytes), whereupon the overall size of the calibration coefficients is:

4(bytes)×29M×10×3=3480 Mbytes(3.4 Gbytes)

Thus, if the display panel, which is the inspection target object, is to be imaged by the camera 40 in a state in which all of the calibration coefficients are stored in the storage unit 52 in advance, first, display unevenness of the display panel is removed by correcting the pixels based on the correction coefficients obtained in advance by illuminating the pixels of the display panel, imaging the pixels, and measuring the luminances of the pixels.

In this state, the display panel is imaged by the camera 40. At the time of imaging, a calibration circuit 53 of the calibration apparatus 50 accesses the storage unit 52 and references the calibration coefficients corresponding to the total number of solid-state imaging elements 41 at the focal length at which the lens 42 is positioned at that time.

The calibration circuit 53 multiplies the referenced calibration coefficients by each pixel in the captured image of the display panel that is formed on the solid-state image sensor 41 due to the display panel being imaged, and calibrates the captured image based on the calibration coefficients. Thus, the sensitivity variations and the like of the solid-state image sensor 41 are calibrated.

Accordingly, when the display panel is imaged by the camera 40 in a state in which display unevenness of the display panel has been removed through correction, due to the fact that the captured image is calibrated, unevenness that does not actually exist on the display panel is not imaged, and the display panel, which is the inspection target, can be favorably imaged.

Thus, due to the fact that it is possible to set the surface of the emission window 24 to a uniform luminance due to the light emission performed by the light-emitting apparatus 10 according to the first embodiment, it is possible to create a suitable calibration coefficient based on the imaged data obtained by imaging the emission window 24 through which the sample light passes.

On the other hand, due to the fact that the luminance with respect to the surface of the bottom surface portion 71 is uniform in a certain range due to the light emission performed by the light-emitting apparatus 60 according to the second embodiment, it is possible to create a suitable calibration coefficient based on the imaged data of the bottom surface portion 71 imaged via the emission window 74.

Due to the fact that the created calibration coefficients are used to calibrate the captured image of the display panel, which is the inspection target image, it is possible to calibrate the captured image by multiplying the suitably-created calibration coefficients by the pixels of the captured image of the display panel formed on the solid-state image sensor 41 due to the display panel being imaged.

Note that the present invention is not limited to the above-described embodiments, and can be modified in various ways without departing from the gist of the invention. In the above-described embodiments, a case is described in which the interior of the case 20 (70) is colored white, but it is also possible to apply a diffuse reflection material to the interior of the case 20 (70), for example.

LIST OF REFERENCE CHARACTERS

10, 60 Light-emitting apparatus
20, 70 Case
22, 72 Top surface portion
24, 74 Emission window
24a Outer edge
25 Covering material
30 Light-emitting portion
32 Light-emitting diode (light-emitting element)
40 Camera
41 Solid-state image sensor
42 Lens
51 Calculation unit
53 Calibration circuit
71 Bottom surface portion
d Distance
$I_1$ Radius
O, O' Central point
R Virtual circle (circumference)

The invention claimed is:

1. A light-emitting apparatus comprising:
a case having a bottom surface portion with a circular outer edge, a top surface portion that is symmetrical to the bottom surface portion, opposes the bottom surface portion, and has a separation distance from the bottom surface portion that is x with respect to a reference diameter, the reference diameter being a diameter of the bottom surface portion, and a circumferential wall portion that is formed into a cylindrical shape that is continuous between the top surface portion and the bottom surface portion;
a plurality of light-emitting elements with a height distance from the bottom surface portion of the case that is set to y with respect to the reference diameter, the light-emitting elements being arranged at equal intervals on an inner circumferential surface in a circumferential direction of the circumferential wall portion; and
an emission window that is provided on the top surface portion, has a diameter set to z with respect to the reference diameter, and allows the light of the light-emitting elements to pass therethrough,
wherein the interior of the case is colored white.

2. The light-emitting apparatus according to claim 1, wherein
the separation distance is set such that its ratio with respect to the reference diameter is 60% or less.

3. The light-emitting apparatus according to claim 1, wherein
the height distance is set such that its ratio with respect to the reference diameter is 45% or less.

4. The light-emitting apparatus according to claim 1, wherein
the diameter of the emission window is set such that its ratio with respect to the reference diameter is 30% or less.

5. The light-emitting apparatus according to claim 1, wherein the light-emitting elements are electrically connected in series.

6. The light-emitting apparatus according to claim 1, wherein
the light-emitting elements are light-emitting diodes that emit red, green, and blue light.

7. A calibration coefficient calculation method for the light-emitting apparatus according to claim 1, the method comprising:
a light emission step of causing the light-emitting elements of the light-emitting apparatus to emit light;
an imaging step of positioning a lens of a camera having a solid-state image sensor at the emission window of the light-emitting apparatus and using the camera to capture a defocused image of the emission window through which sample light emitted by the light-emitting elements passes; and
a calibration coefficient calculation step of calculating a calibration coefficient for calibrating sensitivity of the solid-state image sensor via the lens of the camera based on an output signal output by the solid-state image sensor when the emission window is imaged in the imaging step.

8. The calibration coefficient calculation method according to claim 7, wherein in the imaging step, the emission window is imaged at a plurality of focal lengths of the camera.

9. A method for calibrating a captured image of an inspection target object, wherein based on the calibration coefficient obtained using the calibration coefficient calculation method according to claim 7, the pixels of the captured image of the inspection object, which is formed on the solid-state image sensor due to the target object being imaged using the camera, are calibrated.

* * * * *